(12) United States Patent
Ritter

(10) Patent No.: US 10,973,972 B2
(45) Date of Patent: Apr. 13, 2021

(54) BLOOD TREATMENT MACHINE COMPRISING A HOLLOW FIBER FILTER MODULE FOR HORIZONTAL ARRANGEMENT AS WELL AS HOLLOW FIBER FILTER MODULE AND USE THEREOF

(71) Applicant: B. BRAUN AVITUM AG, Melsungen (DE)

(72) Inventor: Kai-Uwe Ritter, Melsungen (DE)

(73) Assignee: B. BRAUN AVITUM AG, Melsungen (DE)

( * ) Notice: Subject to any disclaimer, the term of this patent is extended or adjusted under 35 U.S.C. 154(b) by 98 days.

(21) Appl. No.: 16/235,023

(22) Filed: Dec. 28, 2018

(65) Prior Publication Data
US 2019/0209767 A1    Jul. 11, 2019

(30) Foreign Application Priority Data
Jan. 11, 2018   (DE) .................... 10 2018 100 568.7

(51) Int. Cl.
*A61M 1/36*    (2006.01)
*B01D 61/24*   (2006.01)
(Continued)

(52) U.S. Cl.
CPC ........ *A61M 1/3635* (2014.02); *A61M 1/1623* (2014.02); *B01D 61/243* (2013.01);
(Continued)

(58) Field of Classification Search
CPC .... A61M 1/3635; A61M 1/1623; A61M 1/16; B01D 61/243; B01D 61/28; B01D 63/02
See application file for complete search history.

(56) References Cited

U.S. PATENT DOCUMENTS 4,148,606 A    4/1979  Morita et al.
4,179,380 A    12/1979 Amicel et al.
(Continued)

FOREIGN PATENT DOCUMENTS

CA    1092515 A    12/1980
DE    2733280 A1    1/1978
(Continued)

OTHER PUBLICATIONS

Extended European Search Report for European Application No. 19151207.8, dated Jun. 24, 2019 with translation, 15 pages.
(Continued)

*Primary Examiner* — Krishnan S Menon

(57) ABSTRACT

An extracorporeal blood treatment machine for carrying out a blood treatment including a machine front on which a hollow fiber filter module is arranged in a horizontal position, which hollow fiber filter module includes a cylindrical housing, a blood chamber having a blood inlet nozzle and a blood outlet nozzle and a solution chamber having a solution inlet nozzle extending transversely to the longitudinal direction of the hollow fiber filter module and a solution outlet nozzle extending transversely to the longitudinal direction of the hollow fiber filter module, the solution chamber being semi-permeably communicated at least in portions with the blood chamber, wherein a height potential is present in the horizontal position between the solution inlet nozzle and the solution outlet nozzle so that drainage of solution is enabled via one of the solution nozzles and evacuation of air bubbles is enabled via an other of the solution nozzles.

3 Claims, 3 Drawing Sheets

(51) Int. Cl.
*B01D 61/28* (2006.01)
*A61M 1/16* (2006.01)
*B01D 63/02* (2006.01)

(52) U.S. Cl.
CPC ............ *B01D 61/28* (2013.01); *B01D 63/02* (2013.01); *B01D 2313/10* (2013.01); *B01D 2313/12* (2013.01); *B01D 2313/20* (2013.01)

(56) References Cited

U.S. PATENT DOCUMENTS

| | | | |
|---|---|---|---|
| 5,058,661 A * | 10/1991 | Oshiyama | A61M 5/44 165/70 |
| 5,441,636 A * | 8/1995 | Chevallet | A61M 1/16 210/232 |
| 5,480,565 A | 1/1996 | Levin et al. | |
| 6,641,731 B1 * | 11/2003 | Heilmann | B01D 46/0004 210/321.79 |
| 7,776,219 B2 | 8/2010 | Brugger et al. | |
| 2013/0020250 A1 | 1/2013 | Keller et al. | |
| 2015/0238676 A1 | 8/2015 | Giordano et al. | |
| 2017/0021082 A1 | 1/2017 | Cook et al. | |
| 2020/0188860 A1 * | 6/2020 | Paul | B01D 67/0011 |

FOREIGN PATENT DOCUMENTS

| | | |
|---|---|---|
| DE | 102011107980 A1 | 1/2013 |
| EP | 0297970 A2 | 1/1989 |
| EP | 0923955 B1 | 6/2008 |
| WO | 2017048224 A1 | 3/2017 |

OTHER PUBLICATIONS

German Search Report for German Application No. 10 2018 100 568.7, dated Jul. 11, 2018, with English translation—15 pages.

* cited by examiner

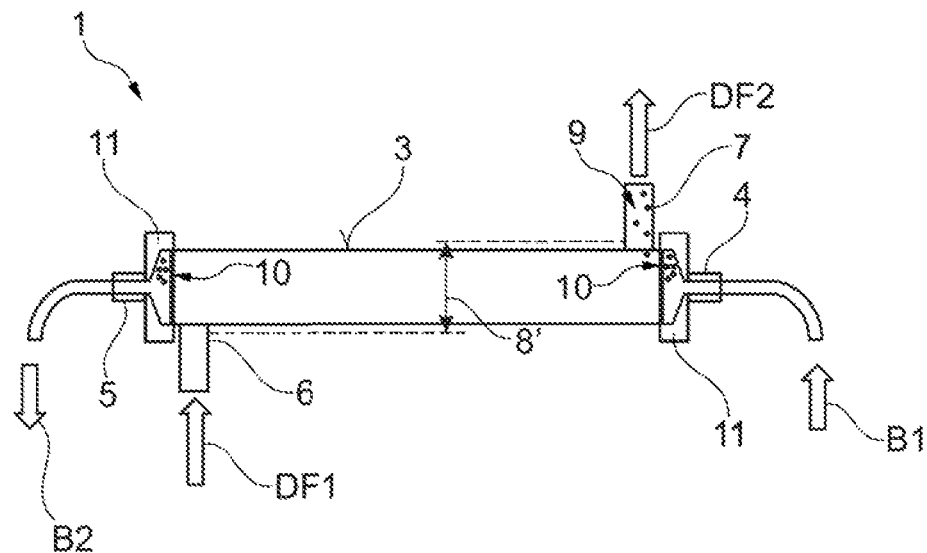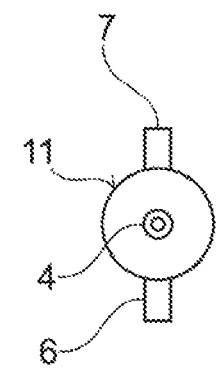
Fig. 1a  Fig. 1b
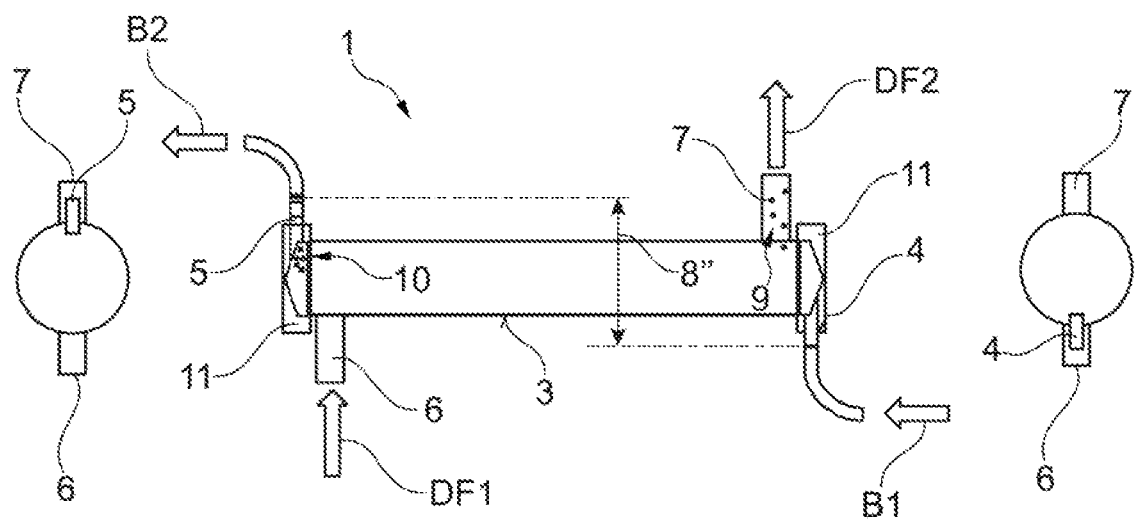
Fig. 2a  Fig. 2b  Fig. 2c

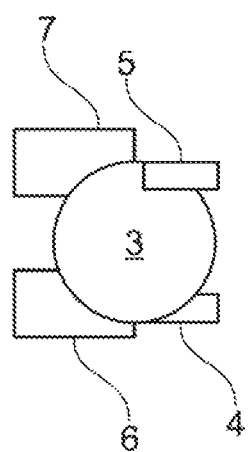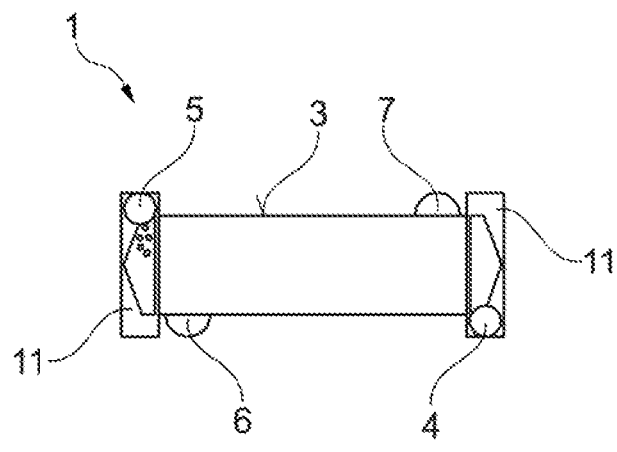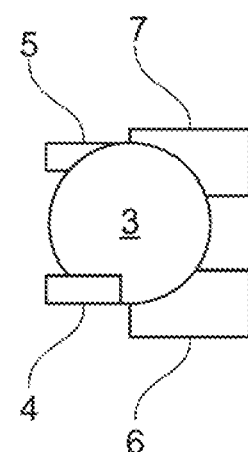
Fig. 5a  Fig. 5b  Fig. 5c
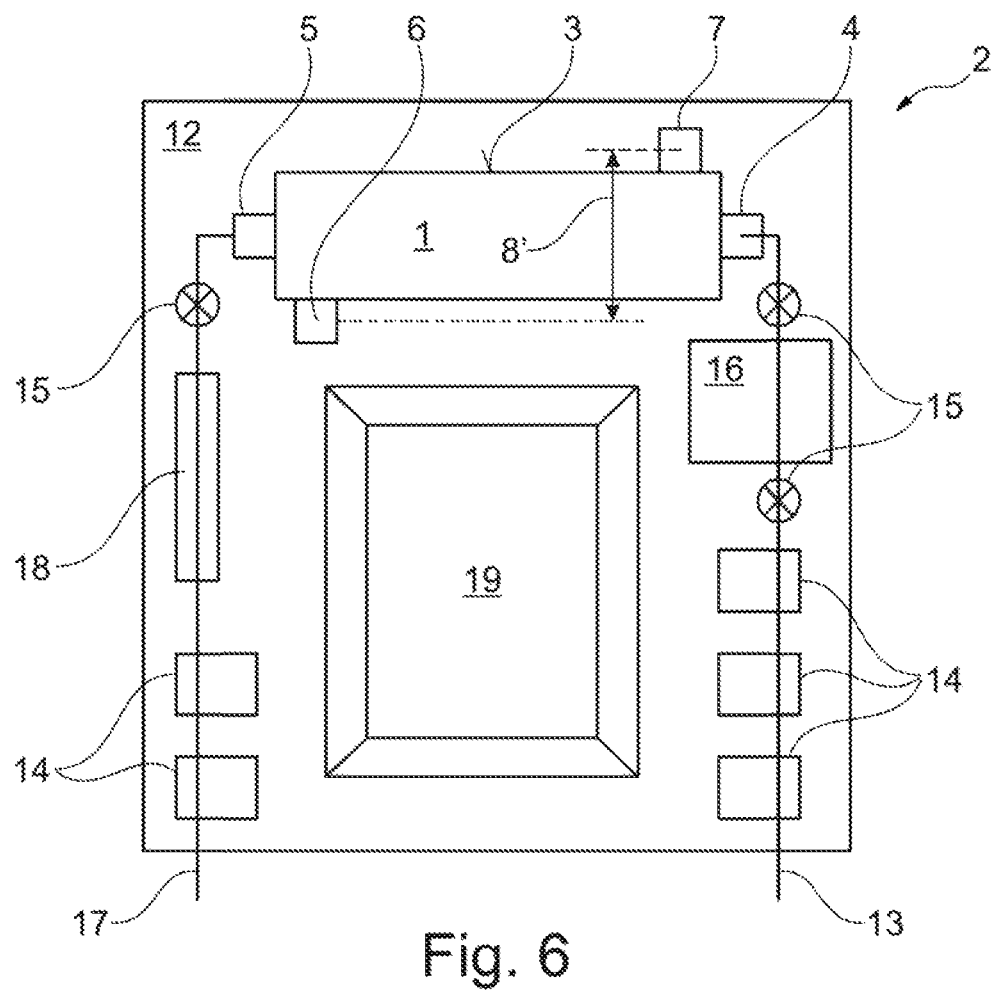
Fig. 6

BLOOD TREATMENT MACHINE COMPRISING A HOLLOW FIBER FILTER MODULE FOR HORIZONTAL ARRANGEMENT AS WELL AS HOLLOW FIBER FILTER MODULE AND USE THEREOF

CROSS REFERENCE TO RELATED APPLICATIONS

This application claims priority to German application DE 10 2018 100 568.7 filed Jan. 11, 2018, the contents of such application being incorporated by reference herein.

FIELD OF THE INVENTION

The present invention relates to an extracorporeal blood treatment machine, such as for carrying out a dialysis treatment, according to the independent claim as well as to a hollow fiber filter module as defined in the dependent claims. Furthermore, the invention relates to use of the hollow fiber filter module. Generic blood treatment machines are employed so that blood treatment/purification can be carried out.

BACKGROUND OF THE INVENTION

The use of hollow fiber filter modules for blood treatment/purification in extracorporeal blood treatment machines is a wide-spread standard. Recently, increasing attention has been drawn to coupling the respective hollow fiber filter modules in a compact arrangement to the blood treatment machine such as a dialysis machine so that the lengths of the lines will be reduced.

For obtaining a compact arrangement it is useful when the hollow fiber filter module can be flexibly attached to the machine at various operating positions.

DESCRIPTION OF THE RELATED ART

The state-of-the-art blood treatment machines and hollow fiber filter modules are almost exclusively optimized for a purely vertical operating position and thus are not flexibly adjustable/variable in their position. US 2015 0238 676 A1 discloses a blood treatment machine according to the independent claim.

EP 0 923 955 B1 discloses a method for manufacturing a dialyzer adapted for vertical arrangement. Accordingly, attention is drawn to optimizing the permeability of the membrane to the effect that (blood) purification can be efficiently carried out.

Further dialyzers on a dialysis machine are known from the documents U.S. Pat. No. 7,776,219 B2 and DE 27 33 280 A1.

Further prior art is known from U.S. Pat. Nos. 4,148,606 A and 5,480,565 A.

Tests made by applicant disclosed drawbacks in the state of the art: The hollow fiber filter modules known from the state of the art are provided and optimized for vertical use in dialysis machines. In the case of use in the horizontal position, they partially exhibit considerable problems. In said position, for example air bubbles may accumulate in the so-called blood chamber and/or in the solution chamber of the hollow fiber module. Air bubbles that are not evacuated impair the purifying capacity of the hollow fiber filter module and therefore have to be avoided. Moreover, draining of the solution (for example after priming) cannot be carried out without any additional expenditure. Consequently, the blood treatment machines and hollow fiber filter modules known from the state of the art are not suited for flexible arrangement which entails a very compact design of the entire blood treatment machine.

SUMMARY OF THE INVENTION

An object underlying the present invention is to eliminate or at least to alleviate the drawbacks from the state of the art and, especially, to disclose such blood treatment machine which combines the advantages of different arrangements—i.e. of the vertical arrangement, the horizontal arrangement and a mixture of both arrangements. Especially, the invention thus focuses on providing a hollow fiber filter module which firstly enables highly efficient blood purification, evacuation/escape of air bubbles and drain of dialysis fluid and which secondly facilitates equipping a blood treatment machine with tubes and the hollow fiber filter module ("disposables") and allows for a high degree of compactness and flexibility.

The invention equally addresses an object to disclose a blood treatment machine which enables reliable blood purification with minimum construction space and a clear and intuitively comprehensible layout of the machine front.

According to aspects of the invention, this object is achieved with a blood treatment machine comprising the features of the independent claim and with a hollow fiber filter module comprising the features of the dependent claims. Further, the use according to the dependent claims solves the afore-mentioned problems.

Advantageous embodiments are the subject matter of the subclaims.

For example, the following further advantages can be derived from this configuration according to aspects of the invention of a hollow fiber filter module and a blood treatment machine:

- the blood treatment machine occupies reduced construction space due to the optimized machine front having the horizontal hollow fiber filter module arrangement and can be flexibly adapted;
- it is more quickly possible to equip the blood treatment machine due to the clearly defined location for each component;
- blood as well as solution tubes have to be designed to be shorter, which firstly (equally) facilitates equipping the blood treatment machine and secondly minimizes the loss of temperature in the respective tubes;
- emptying the hollow fiber filter module from solution (or else blood) is possible without additionally pivoting the hollow fiber filter module;
- air bubbles which (may) occur both in the blood chamber and in the solution chamber are removed (despite the horizontal position);
- efficient blood purification is assisted by the horizontal position.

The subject matter of the invention consequently is an extracorporeal blood treatment machine for carrying out a blood treatment, especially a dialysis treatment, comprising a machine front on which a hollow fiber filter module, especially in the form of a dialyzer, is arranged in a horizontal position. The hollow fiber filter module includes a substantially cylindrical housing, a blood chamber having a blood inlet nozzle and a blood outlet nozzle and a solution chamber having a solution inlet nozzle extending transversely to the longitudinal direction of the hollow fiber filter module and a solution outlet nozzle extending transversely to the longitudinal direction of the hollow fiber filter module, which solution chamber is semi-permeably communicated at least in portions with the blood chamber so as to be adapted for the desired blood treatment.

The term of the housing of the hollow fiber filter module within the scope of the invention shall be broadly interpreted. It has a multi-part structure, for example, of a substantially cylindrical central part and two end caps/dialyzer caps disposed at the respective ends.

The term "transversely" paraphrases, within the scope of this invention, all directions in the transversal plane of the hollow fiber filter module. Especially, the term "transversely" comprises the two directional indications of radial and tangential as well as a mixed form of both vectors.

According to aspects of the invention, in the horizontal position of the hollow fiber filter module between the solution inlet nozzle and the solution outlet nozzle a height potential is provided so that via the one of the two solution nozzles (i.e. via either of the components of the solution inlet nozzle and the solution outlet nozzle) drain of the solution is enabled before or after treatment and via the other one of the two solution nozzles evacuation of air bubbles is enabled during treatment. Preferably, the drain of solution is realized via the solution inlet nozzle and the evacuation of air bubbles is realized via the solution outlet nozzle.

The height potential between two points consequently excels by the fact that between the one point and the other point a potential energy is provided which enables (in the horizontal or even in the partially horizontal position) the solution to be drained. In this way, the invention unifies the effects of efficient air bubble evacuation during treatment and dialyzer drainage after or before the treatment which presently exclude each other.

In other words, the invention can be structurally described so that the hollow fiber filter module of the blood treatment machine has a geometry (namely causing a height potential) in the area of the solution inlet nozzle which is different from that in the area of the solution outlet nozzle. Consequently, the hollow fiber filter module of the blood treatment machine is asymmetrical when mirrored by the transversal plane.

The invention further relates to a hollow fiber filter module comprising a substantially cylindrical housing, a blood chamber including a blood inlet nozzle and a blood outlet nozzle and a solution chamber including a solution inlet nozzle extending transversely to the longitudinal direction of the hollow fiber filter module and a solution outlet nozzle extending transversely to the longitudinal direction of the hollow fiber filter module which solution chamber is semi-permeably communicated at least in portions with the blood chamber. The hollow fiber filter module is arranged/attachable in a horizontal position in an extracorporeal blood treatment machine according to aspects of the invention.

The invention furthermore comprises the use of a hollow fiber filter module for horizontal application in a blood treatment machine.

In an advantageous embodiment of the blood treatment machine, each of the blood inlet nozzle and the blood outlet nozzle of the hollow fiber filter module is disposed to extend transversely, e.g. radially or tangentially, relative to the longitudinal direction of the hollow fiber filter module. This helps to further reduce the required (axial) space of the hollow fiber filter module at the machine front of the blood treatment machine. Equally, said embodiment promotes the operating safety of the hollow fiber filter module as the tubes connected thereto are prevented from kinking.

In this embodiment, further preferably in the horizontal position of the hollow fiber filter module there may be equally provided a height potential between the blood inlet nozzle and the blood outlet nozzle so that via the one of the two blood nozzles blood or priming fluid can be drained and via the other one of the two blood nozzles air bubbles can be evacuated (during treatment). Especially the air bubble evacuation on the blood side constitutes a considerable improvement, as air bubbles are excluded from the semi-permeable exchange through the membrane. Consequently, the invention enables air bubbles to be evacuated/air bubbles to escape both on the solution side and on the blood side—despite an arrangement (at least in portions) extending horizontally.

Further preferred, each of the solution inlet nozzle and the solution outlet nozzle of the hollow fiber filter module is arranged to extend tangentially relative to the (cylindrical) housing, additionally or alternatively to the foregoing embodiment. This generates a swirling solvent flow which helps to improve the cleaning capacity. The tangential inflow on the radial outside further promotes an objective of the invention, as it can be synergistically combined with the arrangement of a height potential.

In another advantageous embodiment, each of the blood inlet nozzle and the blood outlet nozzle (approximately analogously to the solution inlet and solution outlet nozzles) is arranged to extend tangentially relative to the cylindrical housing. This ensures homogenous blood distribution in the dialyzer cap and prevents areas having a low flow velocity. Moreover, the risk of kinking of the blood tubes is drastically reduced. The tangential arrangement of all ports has an advantageous effect on the compact design of the hollow fiber filter module as well.

Especially preferred, the solution inlet nozzle is angularly rotated relative to the solution outlet nozzle in the circumferential direction of the hollow fiber filter module, preferably about 180°, and either of the two solution nozzles (solution inlet nozzle or solution outlet nozzle) points downward in the horizontal position of the hollow fiber filter module. This promotes the drainage caused by the height potential.

An alternative or additionally preferred embodiment excels by the fact that the blood inlet nozzle is angularly rotated relative to the blood outlet nozzle in the circumferential direction of the hollow fiber filter module, preferably about 180°, and either of the two blood nozzles (blood inlet nozzle or blood outlet nozzle) points downward in the horizontal position of the hollow fiber filter module. Thus, the advantages of the solution chamber (such as leakage of air and drainage of fluid) can be conferred upon the blood chamber.

Alternatively to said angular rotation, in a further embodiment the solution inlet nozzle and the solution outlet nozzle are strived for pointing to the same direction (while maintaining the height potential) so as to be capable of being directly coupled to a machine front of the blood treatment machine while avoiding additional tubes. The same direction means that the two nozzles are aligned in parallel, with one nozzle being disposed above and the other nozzle being disposed below the central axis extending along the longitudinal direction of the module. In this way, this embodiment allows to completely dispense with the tubes in which the solution is guided from the blood treatment machine to the hollow fiber filter module and vice versa. The advantages of this configuration are obvious: coupling of the hollow fiber filter module is reduced to simply attaching the dialyzer to the machine front without any tubes being required for this purpose. Furthermore, the use of material is reduced, and the fitting is also improved in terms of time. Finally, also the risk of accident is reduced by the fact that no freely hanging solution tubes are present any more.

Optionally, this embodiment is configured so that the blood inlet nozzle and the blood outlet nozzle point to the same direction which is preferably opposed (by 180°) to the direction of the solution nozzles. This means that all the four nozzles extend in parallel to each other, while the two solution nozzles point to the one direction (i.e. are open toward the one direction) and the two blood nozzles point to the opposite direction. This causes the solution ports to point to the machine so that they can be directly coupled to the latter and causes the blood ports to point to the user, which reduces the length thereof and facilitates fitting.

As an alternative, the blood ports may also point to the same direction as the solution ports (namely, to the machine front). Thus, the port is protected from external impacts and consequently the safety is increased.

Of preference, the shape of the cylindrical housing of the hollow fiber filter module is configured to be compatible with the shape of the machine front or at least with the shape of a dialyzer holder so that the horizontal position of the hollow fiber filter module can be brought about in a defined or centered way. This it is understood to the effect that the machine front and the hollow fiber filter module are adapted to each other to prevent, according to the poka-yoke principle, the hollow fiber filter module from being incorrectly arranged. This facilitates horizontal coupling of the hollow fiber filter module to the machine front and guarantees the desired height potential according to aspects of the invention to be applied. Accordingly, the hollow fiber filter module is adjusted in the way of a patrix-matrix connection.

In accordance with the invention, it is advantageously possible to design the blood tubes that are connected to the blood inlet nozzle and the blood outlet nozzle integrally with the latter. Hence, a blood treatment machine according to aspects of the invention has only to be fitted with a (disposable) comprising the dialyzer, the air separator and the blood tubes, while the dialysis fluid tubes are formed integrally with the machine front.

BRIEF DESCRIPTION OF THE DRAWINGS

The invention is best understood from the following detailed description when read in connection with the accompanying drawings. Included in the drawings are the following figures:

FIG. 1a shows a schematic side view of a hollow fiber filter module according to aspects of the invention in a first embodiment;

FIG. 1b shows a view along the longitudinal axis of the hollow fiber filter module of FIG. 1a;

FIG. 2a shows a view along the longitudinal axis onto the hollow fiber filter module in a second embodiment;

FIG. 2b shows a schematic side view of the hollow fiber filter module of FIG. 2a;

FIG. 2c shows a view along the longitudinal axis of the hollow fiber filter module of FIG. 2a;

FIG. 3b shows a schematic side view of the hollow filter fiber module of FIG. 3a;

FIG. 3c shows a view along the longitudinal axis of the hollow fiber filter module of FIG. 3a;

FIG. 4b shows a schematic side view of the hollow fiber filter module of FIG. 4a;

FIG. 4c shows a view along the longitudinal axis of the hollow fiber filter module of FIG. 4a;

FIG. 5a shows a view along the longitudinal axis of the hollow fiber filter module in a fifth embodiment;

FIG. 5b shows a schematic side view of the hollow fiber filter module of FIG. 5a;

FIG. 5c shows a view along the longitudinal axis of the hollow fiber filter module of FIG. 5a; and FIG. 6 shows a schematic view of a blood treatment machine comprising a horizontally arranged hollow fiber filter module.

DETAILED DESCRIPTION OF THE PREFERRED EMBODIMENTS

Figure 3A:
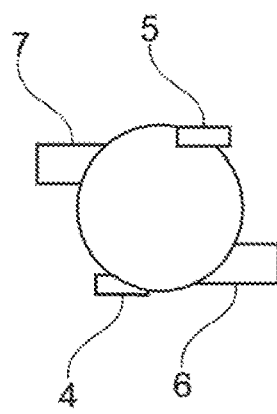
FIG. 3a shows a view along the longitudinal axis of the hollow fiber filter module in a third embodiment.

FIG. 1a illustrates a hollow fiber filter module 1 in the form of a dialyzer which is adapted for horizontal arrangement on a blood treatment machine 2 shown in connection with FIG. 6. The dialyzer has a substantially cylindrical housing 3 surrounding/enclosing/encompassing a blood chamber and a solution chamber which is semi-permeably communicated at least in portions with said blood chamber. Via a blood inlet nozzle 4 blood is supplied to the dialyzer (see arrow B1) which blood (in purified form) is returned and drained via a blood outlet nozzle 5 by the same (see arrow B2). A solution inlet nozzle 6 and a solution outlet nozzle 7 guide/pass the solution or dialysis fluid flow toward and away from the dialyzer (see arrows DF1, DF2).

A height potential 8' is applied between the solution inlet nozzle 6 and the solution outlet nozzle 7. Firstly, this causes a difference in height which enables the dialyzer to be drained via the solution inlet nozzle 6 without any additional change of position of the dialyzer to be present in the horizontal arrangement of the dialyzer between the solution inlet and outlet nozzles 6, 7. Consequently, for draining the dialyzer merely the tube set (e.g. coupled with a Hansen coupling) has to be released from the dialyzer and no additional rotation of the dialyzer or the like is required. This facilitates handling and at the same time reduces the risk of infection, as the dialyzer has only to be touched once, namely, at the beginning. Secondly, said height potential 8' enables air bubbles 9 to leak from the solution chamber via the solution outlet nozzle 7 during operation. Thus, the blood purification carried out by the dialyzer is highly efficient and the problem of stagnant air bubbles in the solution chamber which occurs when using conventional dialyzers in a horizontal position is solved.

The solution inlet and outlet nozzles 6, 7 are aligned to be opposed in the embodiment of FIG. 1a. They are both arranged to extend radially relative to the housing 3 and are angularly offset against each other by 180° in the circumferential direction. In the horizontal operating position, the solution inlet 6 is arranged to point downward and the solution outlet 7 is arranged to point upward. In this way, the afore-mentioned effect of improved drainage with simultaneous leakage of air bubbles from the solution chamber is intensified.

Apart from the (substantially) cylindrical portion on which the nozzles 6, 7 are arranged, the housing 3 also comprises a dialyzer cap 11 on each of the two end faces. The respective dialyzer cap 11 forms the blood inlet and blood outlet nozzles 4, 5 which in the present case are arranged to extend in the axial direction of the dialyzer. Of preference, the dialyzer cap 11 is configured so that the air bubbles 10 in the blood chamber can attach to or accumulate on the same without impairing the blood purification. In contrast to the air bubbles 9 present in the solution chamber, such air bubbles 10 present in the blood chamber in the first embodiment cannot be or are difficult to be evacuated and, consequently, attach in the respective end area of the housing 3, i.e. in the area of the dialyzer caps 11.

FIG. 1b depicts the dialyzer of FIG. 1a along its longitudinal axis wherefrom the 180° arrangement of the nozzles 6, 7 relative to each other is resulting. The blood inlet nozzle 4 configured by the dialyzer cap 11 is perpendicular to the imaginary line connecting the solution inlet nozzle 6 in the present figure to the solution outlet nozzle 7.

A second embodiment is shown in the FIGS. 2a to 2c. FIG. 2b illustrates the dialyzer of said embodiment in the side view, while in FIG. 2a it is shown in the perspective of a viewer on the one side ("left") and in FIG. 2c it is shown in the perspective of a viewer on the other side ("right") along its longitudinal axis. The essential components of this embodiment are known from the embodiment explained in connection with FIG. 1a and now will not be shown in detail once again to avoid repetitions.

The difference of said second embodiment from the first embodiment consists in the fact that the blood inlet nozzle 4 just as the blood outlet nozzle 5 are arranged to extend radially (and no longer axially) relative to the housing 3. Thus, apart from the height potential 8' prevailing in the solution chamber, a height potential 8" is also realized in the blood chamber. This saves axial construction space and reduces the risk of kinking of the respective tubes. Moreover, now leakage/removal of the air bubbles 10 in the blood chamber is possible just as leakage/removal of the air bubbles 9 in the solution chamber.

As is evident from the FIGS. 2a and 2c, the respective blood inlet and blood outlet nozzles 4, 5 are arranged to be angularly offset against each other by 180° in the circumferential direction. The solution inlet and solution outlet nozzles 6, 7 correspond, as to their position in the circumferential direction (not in the axial direction, see FIG. 2b), to the position of the blood inlet and blood outlet nozzles 4, 5. Following the counter-flow principle common in dialyzers, the solution inlet nozzle 6 and the blood outlet nozzle 5 are arranged in an end area of the housing 3, whereas the solution outlet nozzle 7 and the blood inlet nozzle 4 are arranged in the other opposed end area. This applies to all embodiments disclosed here.

Figure 3C:
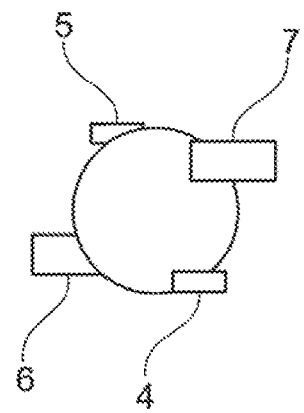
Figure 3B:
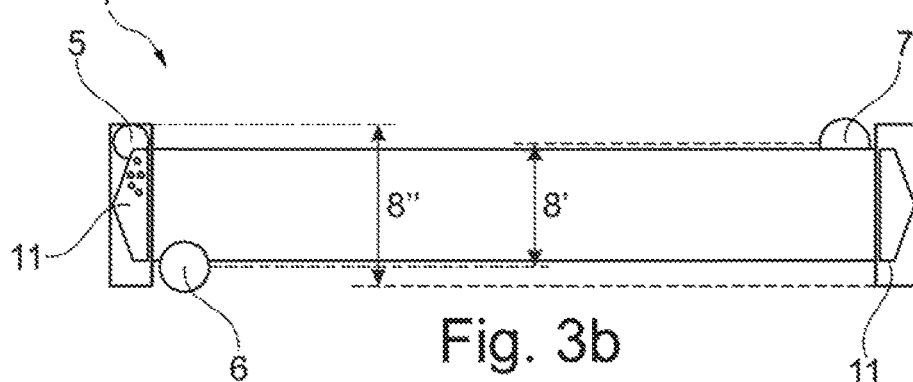

A third embodiment is illustrated in the FIGS. 3a to 3c. FIG. 3b depicts the dialyzer of said embodiment in the side view, while in FIG. 3a it is shown in the perspective of a viewer on the one side ("left") and in FIG. 3c it is shown in the perspective of a viewer on the other side ("right") along its longitudinal axis. The essential components of this embodiment are known from the preceding embodiments and now will not be described in detail once again to avoid repetitions.

The third embodiment differs from the embodiments of the FIGS. 1 and 2 by the fact that all nozzles 4, 5, 6, 7 are arranged to extend tangentially relative to the housing 3. Consequently, the blood inlet nozzle 4 is not visible in the view from FIG. 3b. The blood drain from the blood outlet nozzle 5 in FIG. 3b steps out of the plane of projection in perspective, while the solution intake into the solution inlet nozzle 6 extends into the plane of projection.

Said tangential inflow and outflow promotes swirling of the fluid flows and has a positive effect on the purification rate of the dialyzer. Of preference, the tangential arrangement refers to the (outer) periphery of the dialyzer. As is evident, for example, from the FIGS. 3a and 3c, the inventive idea also comprises those tangential arrangements which are tangentially arranged not fully outside but approximately up to half the radius.

In FIGS. 3a and 3c, all nozzles 4, 5, 6, 7 are visible from the perspective of the respective viewer viewing along the longitudinal axis of the dialyzer. In the present embodiment, the blood nozzles 4, 5 just as the solution nozzles 6, 7 are arranged to be diagonally opposed to each other. Hence, apart from the height potential 8', 8" also different inlet and outlet positions in width are obtained.

At the one end of the dialyzer, the nozzles 5 and 6 protrude transversely/tangentially in one direction (out of the plane of projection), whereas at the other end of the dialyzer the nozzles 4 and 7 protrude transversely/tangentially in the other direction (into the plane of projection).

The amount of the blood-side height potential 8" exceeds the amount of the solution-side height potential 8', as the blood nozzles 4, 5 can be arranged further outside because the dialyzer caps 11 protrude radially further than the central part of the housing 3. Deviations are possible and may be caused by the position of the solution nozzles 6, 7 and, respectively, the blood nozzles 4, 5.

Figure 4A:
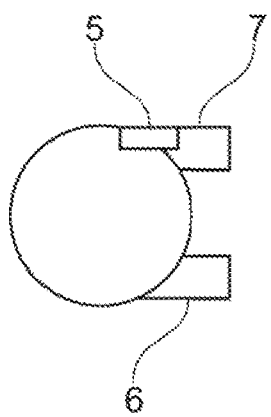
FIG. 4a shows a view along the longitudinal axis of the hollow fiber filter module in a fourth embodiment.
Figure 4C:
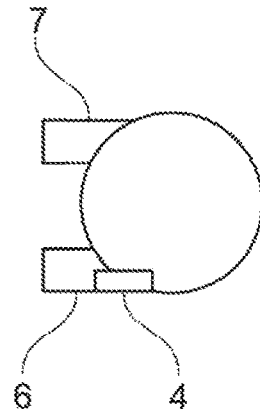
Figure 4B:
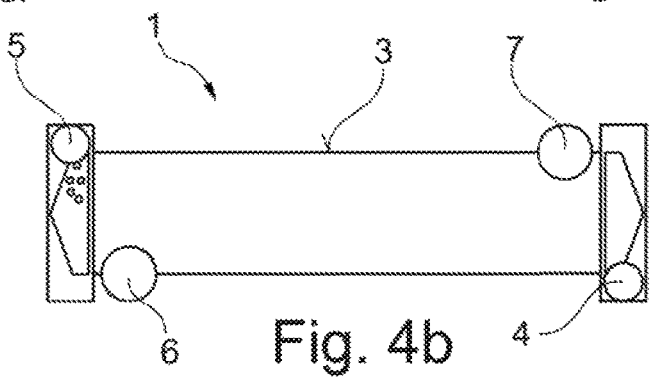

Another embodiment is illustrated in the FIGS. 4a to 4c. FIG. 4b illustrates the dialyzer of said embodiment in the side view, while in FIG. 4a it is shown in the perspective of a viewer on the one side ("left") and in FIG. 4c it is shown in the perspective of a viewer on the other side ("right"). The essential components of this embodiment are known from the preceding embodiments and now will not be described in detail once again to avoid repetitions.

The embodiment of FIG. 4 differs from that of FIG. 3 in that all tangentially extending nozzles 4, 5, 6, 7 are projecting on/from the same side of the dialyzer while extending parallel to each other. Thus, the dialyzer of said embodiment is very compact, as can be inferred from the FIGS. 4a and 4c. The dialyzer can optionally be coupled to a machine front 12 shown in connection with FIG. 6 so that all ports are pointing to the latter (which causes a short tube length) or else are pointing away therefrom (which facilitates fitting of the machine).

Another embodiment is illustrated in the FIGS. 5a to 5c. FIG. 5b shows the dialyzer of this embodiment in the side view, while in FIG. 5a it is shown in the perspective of a viewer on the one side ("left") and in FIG. 5c it is shown in the perspective of a viewer on the other side ("right") along its longitudinal axis. The essential components of this embodiment are known from the preceding embodiments and will not be described in detail once again to avoid repetitions.

The distinguishing feature of the embodiment of FIG. 5 as compared to those of the afore-presented embodiments consists in that the blood nozzles 4, 5 are arranged to point to the one direction while the solution nozzles 6, 7 are arranged to point to the opposite direction. Preferably, the solution nozzles 6, 7 point to the machine front 12 (see FIG. 6) so that they can be directly coupled to the treatment machine 2 without any tubes being interconnected, as explained already in the foregoing.

FIG. 6 schematically shows a blood treatment machine 2. The machine front 12 is configured to be optimized as to space which is significantly enabled due to the horizontal arrangement of the hollow fiber filter module 1. An arterial tube 13 taking blood from a patient initially passes safety units 14 (such as a shut-off clip and/or an air detector), pressure pick-ups 15 as well as a pump 16 (preferably in the form of a peristaltic pump), before it supplies, when connected to the blood inlet nozzle 4, blood to be purified to the hollow fiber filter module 1.

After purification (on the counter-flow principle) the blood leaves the blood outlet nozzle 5 into a venous tube 17 which returns the blood (after further detectors and an air separator 18) in a purified form to the patient. A central area 19 on the machine front 12 is kept free for arranging a heparin pump, for example, and for various interfaces (ports and switches).

The horizontal arrangement of the hollow fiber filter module 1 enables first the blood tubes 13, 17 to extend in horseshoe shape. Thus, the latter are kept as short as possible, which, apart from savings of material and space, also has the positive effect of reduced blood temperature loss in the extracorporeal purification. Moreover, the horizontal arrangement enables the solution inlet nozzle 6 and the solution outlet nozzle 7 to be coupled directly to the machine front while realizing the height potential 8' so that solution/dialysis fluid tubes can be completely dispensed with.

Finally, it shall be mentioned that the blood tubes (throughout all embodiments) are either configured to be releasable from the dialyzer, for example via Luer locks, or else are configured integrally with the dialyzer caps 11 to further reduce the number of disposables.

The invention claimed is:

1. An extracorporeal blood treatment machine for carrying out a blood treatment comprising:
   a machine front; and
   a hollow fiber filter module arranged in a horizontal position on the machine front; wherein the hollow fiber filter module has:
   a cylindrical housing having a first end, a second end opposite the first end, and a central longitudinal axis extending from the first end to the second end,
   a blood chamber having a blood inlet nozzle and a blood outlet nozzle, and
   a solution chamber having a solution inlet nozzle extending transversely to a longitudinal direction of the hollow fiber filter module and a solution outlet nozzle extending transversely to the longitudinal direction of the hollow fiber filter module, the solution chamber being semi-permeably communicated at least in portions with the blood chamber, wherein in the horizontal position of the hollow fiber filter module a first height potential is present between the solution inlet nozzle and the solution outlet nozzle so that via one of the two solution nozzles drainage of solution is enabled and via another of the two solution nozzles evacuation of air bubbles is enabled,
   the blood outlet nozzle and solution inlet nozzle extending radially relative to the longitudinal axis from the first end, with the blood outlet nozzle angularly offset from the solution inlet nozzle by 180° in a circumferential direction,
   the blood inlet nozzle and solution outlet nozzle extending radially relative to the longitudinal axis from the second end, with the blood inlet nozzle angularly offset from the solution outlet nozzle by 180° in the circumferential direction, and
   the blood inlet nozzle, blood outlet nozzle, solution inlet nozzle and solution outlet nozzle extending parallel to one another in a common plane passing through the longitudinal axis,
   wherein in the horizontal position of the hollow fiber filter module a second height potential is present between the blood inlet nozzle and the blood outlet nozzle so that via one of the two blood nozzles drainage of blood is enabled and via another of the two blood nozzles evacuation of air bubbles is enabled.

2. The extracorporeal blood treatment machine according to claim 1, wherein the solution inlet nozzle is angularly rotated relative to the solution outlet nozzle in the circumferential direction of the hollow fiber filter module and one of the two solution nozzles points downward in the horizontal position of the hollow fiber filter module and/or the blood inlet nozzle is angularly rotated relative to the blood outlet nozzle in the circumferential direction of the hollow fiber filter module and one of the two blood nozzles points downward in the horizontal position of the hollow fiber filter module.

3. The extracorporeal blood treatment machine according to claim 1, wherein the cylindrical housing is horizontally coupled to the machine front such that the horizontal position of the hollow fiber filter module is centered on the machine front.

* * * * *